United States Patent [19]

Clark, III

[11] 3,996,938

[45] Dec. 14, 1976

[54] EXPANDING MESH CATHETER

[76] Inventor: William T. Clark, III, No. 6 Davis Blvd., New Orleans, La. 70121

[22] Filed: July 10, 1975

[21] Appl. No.: 594,706

[52] U.S. Cl. .................................................. 128/348
[51] Int. Cl.² .......................................... A61M 25/00
[58] Field of Search ............... 128/303 R, 341, 342, 128/343, 344, 348

[56] References Cited

UNITED STATES PATENTS

| 2,836,181 | 5/1958 | Tapp | 128/348 X |
|---|---|---|---|
| 3,435,826 | 4/1969 | Fogarty | 128/348 |
| 3,509,883 | 5/1970 | Dibelius | 128/348 |

FOREIGN PATENTS OR APPLICATIONS

| 592,182 | 4/1925 | France | 128/341 |
|---|---|---|---|
| 26,119 | 1907 | United Kingdom | 128/341 |
| 1,205,743 | 9/1970 | United Kingdom | 128/343 |

*Primary Examiner*—Channing L. Pace

[57] ABSTRACT

The diameter of a normally cylindrical mesh on the distal end of a flexible catheter is increased by a manually operated plunger so as to remove a clot from the vessel as the catheter is withdrawn.

3 Claims, 4 Drawing Figures

EXPANDING MESH CATHETER

FIELD OF INVENTION

Surgery, Cannula, Catheter.

OBJECTS

It is the purpose of this invention to provide a new and effective means of removing organized, cross-linked blood clots (thrombi) from the human vascular system. It is a further object of this invention to provide a tool for the physician which is relatively safe, reliable, and simple to operate and which can be operated in such manner that surgery may be unnecessary for thrombectomy, endarterectomy, and similar procedures.

A particularly useful application of this invention is in the removal of fibrin clots formed as a consequence of vascular prostheses such as the arterio-venous shunt used with hemodialysis and other procedures. Furthermore, this invention may help to prevent the recurrence of such thrombi.

At present, thrombosis is conventionally treated by surgical intervention if the affected vessel is a very large or important one, or if vital circulation is affected. If the thrombosed vessel is a small one, it is usually sacrificed, leaving the circulation to other vessels. With the arterio-venous shunt and many other conditions, however, the auxiliary vessels soon become exhausted and no more shunt sites or auxiliary vessels are available. With the chronic renal patient, this quickly becomes a very serious problem.

If the thrombus is very recent, it can sometimes be partly removed by a balloon catheter. However, at present, surgery will eventually be required, because the balloon catheter cannot effectively remove firmly attached clots, or prevent their recurrence. Further, because the balloon catheter must be inflated, there is the danger that a foreign medium used to inflate the balloon may be introduced into the vascular system, which may cause infection, tissue reaction, or air-embolism. By contrast, the present invention is operated by direct mechanical linkage and introduces nothing into the vascular system but the catheter itself. The mechanical linkage also offers valuable sensory feedback to the physician's fingers which assists precise operation of the instrument.

These and other objects will be apparent from the following drawing, in which.

Figure 1:
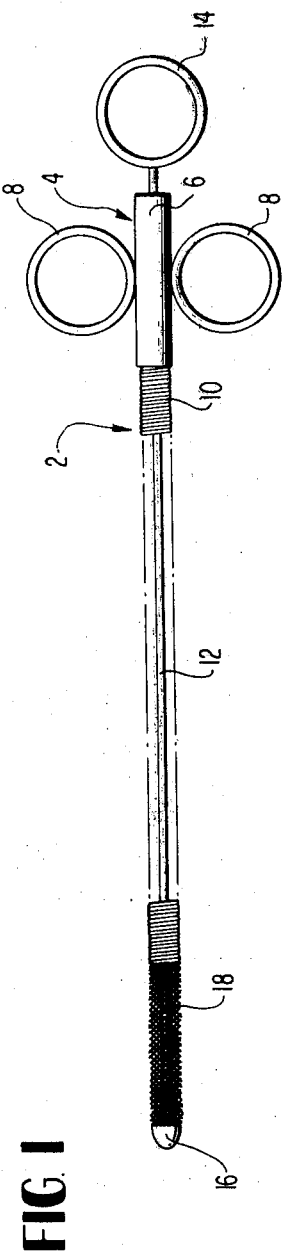
FIG. 1 is an elevational view of the catheter in the position in which it is inserted into a vessel.

Referring now to the drawing in which like reference numerals denote similar elements, the catheter 2 is comprised of a guide tube 4 having a barrel portion 6 with finger rings 8 secured thereto and an elongate flexible portion 10 preferably, although not necessarily, formed of tightly wound spring wire. A flexible plunger wire 12 slidably extending through tube 4 has on its outer end a thumb ring 14, and on the other end, which is the distal end of the catheter, there is secured a round ended tip 16, which is generally of bullet shape.

Figure 2:
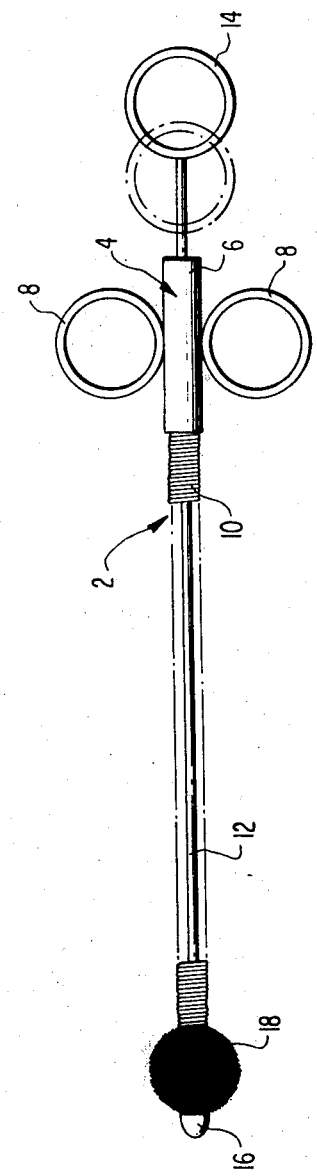
FIG. 2 is a view similar to FIG. 1, but showing the catheter with the mesh expanded.
Figure 4:
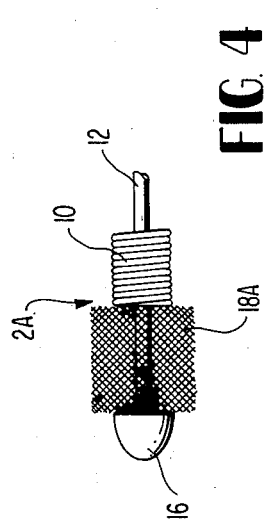
Figure 3:
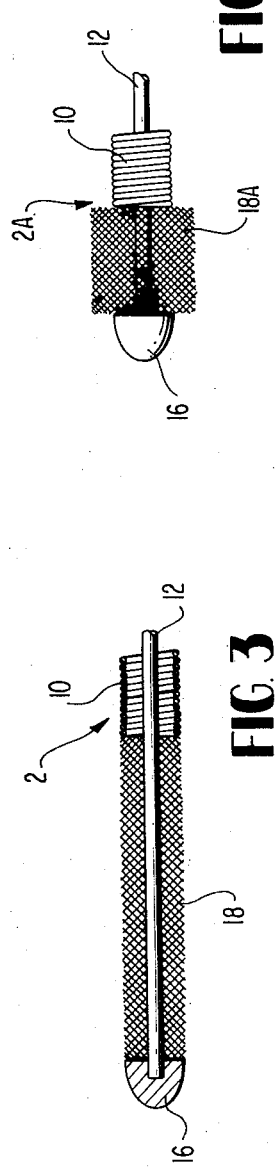
FIG. 3 is a fragmentary cross section showing the details of the distal end; and, FIG. 4 is a fragmentary elevational view of the distal end of a modified form of the catheter shown in FIGS. 1–3.

Between the tip 16 and the end of the flexible portion 10 of the guide tube is a mesh sleeve 18. The ends of the sleeve 18 are secured to the round ended tip 16 and the flexible portion 10 of the guide tube so that the mesh cannot be accidently dislodged during use, and likewise the round ended tip 16 is secured to the end of the flexible plunger wire 12. The mesh sleeve 18 is preferably a tubular braid of, for example, tinned copper, stainless steel, or silver. It is normally tubular as shown in FIG. 1, but when the thumb ring 14 is pulled back so as to draw the flexible plunger wire 12 back, the mesh is pressed between its ends so that it assumes an expanded condition, as in FIG. 2. The catheter 2A fragmentarily illustrated in FIG. 4 is the same as that illustrated in FIGS. 1–3, except in that the mesh in sleeve 18A is a finer weave than that of sleeve 18. It has been found that a mesh of relatively course weave will expand more whereas the finer weave meshes are more dimensionally stable. In either case, the mesh sleeve may be removable and replaceable, but, in any event, its ends should be securely fastened to the rounded tip end 16 and the end of the flexible portion 10 of the guide tube 4.

In operation, the catheter enters the vessel in its FIG. 1 condition below the clot with the mesh extended to its contracted position. The catheter passes through or around the clot following the path of least resistance. At a point above the clot or a narrowed part of the vessel, the mesh is then expanded to maintain approximate contact with the clot or vessel wall. The catheter is then withdrawn, carrying the clot with it. At the same time, the mesh cleans and smooths irregularities on the vessel wall, thereby helping prevent the recurrence of thrombosis.

The materials used to construct the catheter should be readily sterilizable, non-pyrogenic, and free of tissue reaction. Stainless steel and silver have been found particularly suitable, as they can be autoclaved. However, many other materials, including plastics inert to body fluids, will also be found suitable.

The construction of the instrument is determined by its intended use and the size of the vessels. For example, a convenient size for shunt-declotting in the limbs would have a mean diameter of approximately one-sixteenth inch. A tubular mesh of one hundred wires of 0.004 inch diameter woven to a tube of one-sixteenth inch will expand to one-quarter inch. Of course, many types of expandable mesh may be used; tubular braid has been found particularly suitable. Biased woven cloth may be used. Physiological-inert polymers may also be employed, such as woven polyester mesh or sterilizable reticulated polymer foam. Other modifications can be made without departing from the principle of the invention. For example, the flexible portion 10 of the guide tube, instead of being formed of wound spring wire, could be replaced by a flexible-polymer tube. Likewise, although the catheter as illustrated is designed for finger operation, it could be readily designed for hand operation. It is desirable that the entire instrument be radiopaque.

This invention has been extensively clinically tested, and can affectively remove blood clots which are completely resistant to the balloon catheter, thereby frequently eliminating the need for surgery.

I claim:

1. A catheter comprising
    a guide tube having an elongate flexible portion,
        flexible plunger slidably disposed in said tube, and having one end portion extending outwardly beyond an end of the flexible portion of said guide tube, a rounded tip member on the outer end of said plunger, a mesh sleeve surrounding said outwardly extending end portion of said plunger and having opposite ends respectively connected to said tip member and said end of said guide tube, and means on the other end of said tube and the other end of said plunger for manipulating the same and for pulling said tip towards said guide tube whereby to expand said mesh sleeve.

2. A catheter as claimed in claim 1, said mesh sleeve being comprised of tubular braid.

3. A catheter as claimed in claim 1, said tip being generally of bullet shape.

* * * * *